United States Patent
Richard et al.

(10) Patent No.: US 11,426,547 B2
(45) Date of Patent: Aug. 30, 2022

(54) MONITORING OR VENTILATION APPARATUS FOR CARDIOPULMONARY RESUSCITATION WITH DETERMINATION OF AN AIRWAY OPENING INDEX

(71) Applicant: Air Liquide Medical Systems, Antony (FR)

(72) Inventors: Jean-Christophe Richard, Anotny (FR); Marceau Rigollot, Montrouge (FR); Bilal Badat, Montrouge (FR)

(73) Assignee: Air Liquide Medical Systems, Antony (FR)

( * ) Notice: Subject to any disclaimer, the term of this patent is extended or adjusted under 35 U.S.C. 154(b) by 499 days.

(21) Appl. No.: 16/600,918

(22) Filed: Oct. 14, 2019

(65) Prior Publication Data

US 2020/0114103 A1 Apr. 16, 2020

(30) Foreign Application Priority Data

Oct. 15, 2018 (FR) ...................................... 1859509

(51) Int. Cl.
- *A61M 16/00* (2006.01)
- *A61B 5/083* (2006.01)
- *A61B 5/00* (2006.01)

(52) U.S. Cl.
CPC ......... *A61M 16/024* (2017.08); *A61B 5/0836* (2013.01); *A61B 5/742* (2013.01); (Continued)

(58) Field of Classification Search
CPC .................................................. A61B 5/0836
See application file for complete search history.

(56) References Cited

U.S. PATENT DOCUMENTS

| 2012/0016279 A1 | 1/2012 | Banville et al. |
| 2016/0133160 A1 | 5/2016 | Packer et al. |
| 2016/0287170 A1 | 10/2016 | Ronen et al. |

FOREIGN PATENT DOCUMENTS

| AU | 2013 377427 | 9/2015 |
| AU | 2015 202627 | 12/2015 |

(Continued)

OTHER PUBLICATIONS

French Search Report for corresponding FR 1859509, dated Jun. 26, 2019.

*Primary Examiner* — Margaret M Luarca
*Assistant Examiner* — Cana A Gallegos
(74) *Attorney, Agent, or Firm* — Allen E. White (57) ABSTRACT

The invention relates to a monitoring and/or respiratory assistance apparatus that can be used during a cardiopulmonary resuscitation (CPR) with successive chest compressions of duration (dt) performed on the patient and with relaxations, said apparatus comprising a $CO_2$ content measurement sensor (10) a graphical user interface (14), and signal-processing system (11) configured to process the $CO_2$ content measurement signals in such a way as to determine at least one maximum $CO_2$ content value (Vmax) and at least one minimum $CO_2$ content value (Vmin), during at least one duration (dt) of at least one chest contraction, and then to calculate at least one airway opening index AOI or mean index $AOI_{mean}$ on the basis of the $CO_2$ content values. Said one or more indices are displayed on the GUI in the form of numerical values or graphical representations, especially curves or pictograms.

12 Claims, 3 Drawing Sheets

(52) U.S. Cl.
CPC .... *A61M 16/0003* (2014.02); *A61M 16/0051* (2013.01); *A61M 2230/432* (2013.01)

(56) References Cited

FOREIGN PATENT DOCUMENTS

| | | |
|---|---|---|
| AU | 2014 255597 | 3/2017 |
| EP | 2 947 328 | 11/2015 |
| EP | 2 954 213 | 12/2015 |
| EP | 3 093 498 | 11/2016 |
| EP | 2 102 504 | 2/2017 |
| EP | 2 986 856 | 9/2019 |
| WO | WO 2010 059049 | 5/2010 |
| WO | WO 2014 072981 | 5/2014 |

MONITORING OR VENTILATION APPARATUS FOR CARDIOPULMONARY RESUSCITATION WITH DETERMINATION OF AN AIRWAY OPENING INDEX

CROSS REFERENCE TO RELATED APPLICATIONS

This application claims the benefit of priority under 35 U.S.C. § 119 (a) and (b) to French Patent Application No. 1859509, filed Oct. 15, 2018, the entire contents of which are incorporated herein by reference.

BACKGROUND

The invention relates to a monitoring and/or respiratory assistance apparatus that can be used during a cardiopulmonary resuscitation (CPR) comprising successive chest compressions performed on a patient, in particular a medical ventilator for delivering a respiratory gas to the patient during the CPR, that is to say a patient in cardiac arrest on whom cardiac massage is performed with alternating chest compression and relaxation, with determination and optional display of the AOI (i.e. Airway Opening Index) of the patient or of a mean AOI.

Medical apparatuses for mechanical ventilation, also called respiratory assistance apparatuses or medical ventilators, are currently used to deliver respiratory gas, for example oxygen-enriched air or non-oxygen-enriched air, to certain patients suffering from respiratory problems. The delivery of the respiratory gas to the patient is currently effected by means of a motorized and controlled microblower (also called a turbine or compressor), as is described in particular by EP-A-3093498, EP-A-2947328, EP-A-2986856, EP-A-2954213 or EP-A-2102504.

It is known to monitor the gaseous compounds present in the gas administered to the patients, either using a monitoring apparatus or using a ventilator equipped with an indicator. In particular, it may be very useful to monitor the $CO_2$ resulting from the pulmonary gas exchanges, that is to say $CO_2$ produced by the patient's metabolism, conveyed to the lungs by the blood stream, then discharged during exhalation by the patient. Thus, $etCO_2$, standing for End Tidal $CO_2$ or $CO_2$ at the end of exhalation, corresponds to the measurement of the $CO_2$ fraction exhaled in the gases collected during the exhalation of an individual, whether the inhalation is natural or assisted, that is to say obtained by mechanical ventilation. The document US-A-2016/0287170 teaches such monitoring of $etCO_2$.

During cardiopulmonary resuscitation (CPR) performed on a person in cardiopulmonary arrest, with use of cardiac massage, the alveolar $CO_2$, which depends not only on the ratios between ventilation and pulmonary perfusion but also on the quantity of $CO_2$ generated by the cell metabolism, is a very useful parameter for allowing the first responder, for example a physician, to judge the efficacy of the CPR.

In theory, the more effective the CPR, the greater the cardiac output generated by the chest compressions, and the larger the quantity of $CO_2$ returned to the lungs.

For this reason, monitoring of the $etCO_2$, which indirectly reflects the alveolar $CO_2$, is increasingly used to monitor the CPR non-invasively, that is to say to provide information to the first responder while performing the cardiac massage, i.e. alternating chest compressions (CC) and relaxations.

The graphical representation of the variations of the $CO_2$ content in the respiratory gases of a patient over time (in seconds) is called a capnogram.

During CPR on a patient in cardiorespiratory arrest (CRA), the capnogram is very different from that obtained on a patient who is not in CRA, for several reasons, particularly:

The chest compressions generate movements of small volumes of gas, which disturb the capnogram between two ventilation cycles. Oscillating lines are therefore often observed, since the maximum $CO_2$ value on each chest compression does not cease to vary.

The ventilation/perfusion ratios, which are a reflection of the respiratory physiology, are very considerably modified. Moreover, the small gas segments mobilized by the chest compressions may pass the sensor several times. The maximum concentration observed during each chest compression is thus often far removed from the real alveolar concentration.

Dynamic behaviour of opening and closing of the small airways has been reported. This phenomenon compromises the exchanges of gas and therefore the interpretation of the $CO_2$ concentrations during CPR. More precisely, during CPR, the small intrapulmonary airways may close, thereby modifying the exhaled $CO_2$ signal seen by the capnograph probe.

It will thus be appreciated that $etCO_2$ as measured currently, that is to say during each chest compression (CC) (also called chest contraction), does not permit a reliable approximation of the alveolar $CO_2$, although the alveolar $CO_2$ is important because it may reflect the quality of the CPR and therefore of the massage.

In other words, measurement and monitoring of the $CO_2$ that does not take account of all or some of these factors, in particular the impact of the ventilation performed on the patient in cardiac arrest and the variability of the $CO_2$ signal between two machine cycles, makes the use of this $CO_2$ measurement somewhat unreliable or even unusable.

Moreover, the current solutions involving the monitoring of $etCO_2$ are adapted to the $CO_2$ variations produced by breathing, whether mechanical or spontaneous. The frequencies involved are of the order of 10 to 40 c/min. The algorithms and mechanisms used are adapted to these frequencies and to small variations of the $CO_2$ between two respirations of the patient.

Now, during CPR, the frequencies of the chest compressions are close to 100 c/min, the volumes of gas that are mobilized are small, and the gas flowrates are considerable and irregular. Moreover, the problem of the dead space mentioned above adds to these difficulties since, on account of the chest compressions, a same fraction of gas may be analysed several times by the $CO_2$ sensor, if there is no rinsing or purging of the dead space.

Under these conditions, the $etCO_2$ value displayed by the current ventilators or monitors is refreshed at an inadequate frequency, since they attempt to follow the evolution of the $CO_2$ at the massage frequency, i.e. 100 c/min. In other words, the $etCO_2$ values displayed by the current ventilators or monitors are not representative of a $CO_2$ concentration linked to the patient's metabolism, since the origin of the gas analysed is not guaranteed, that is to say the values measured are often erroneous since they do not reflect, or they reflect very poorly, the concentration of alveolar $CO_2$.

Mention may be made of the documents WO-A-14072981, US-A-2016/0133160 and US-A-2012/0016279, which propose methods for monitoring the $CO_2$ content in the gases exhaled by a patient undergoing CPR.

The problem therefore is to make available an improved monitoring and/or respiratory assistance apparatus, such as a monitor or a ventilator, that can be used during a cardiopulmonary resuscitation (CPR) with cardiac massage comprising successive chest compressions (CC) of duration (dt), performed on the patient, and successive relaxations, by which the medical team is informed in real time of the opening or non-opening of the airways and thus knows whether or not the successive chest compressions performed generate a ventilation flowrate.

The solution of the invention therefore concerns a monitoring and/or respiratory assistance apparatus that can be used during a cardiopulmonary resuscitation (CPR) comprising successive chest compressions (CC) of duration (dt), performed on the patient, and relaxations, in particular an apparatus chosen from among the assisted ventilation apparatuses comprising a source of respiratory gas, cardiac monitors, and cardiac monitors/defibrillators, said apparatus comprising:

means for measuring the $CO_2$ content in order to perform measurements of the concentration of $CO_2$ produced by the patient during the cardiopulmonary resuscitation (CPR), and to supply $CO_2$ content measurement signals to signal-processing means, signal-processing means configured to process the $CO_2$ content measurement signals originating from the $CO_2$ content measurement means, and at least one graphical user interface (GUI), characterized in that the signal-processing means are configured to:

a) determine at least one maximum $CO_2$ content value (Vmax) and at least one minimum $CO_2$ content value (Vmin), during at least one duration (dt) of at least one chest compression, and b) calculate at least:

one airway opening index AOI such that: AOI=(Vmax−Vmin)/Vmax or a mean index $AOI_{mean}$ on the basis of several successive opening indices AOI obtained during the durations (dt) of n successive chest compressions (with n>1), and c) transmit to said graphical user interface at least one index value AOI or at least one mean index value $AOI_{mean}$, and the graphical user interface is configured to display said at least one index value AOI or mean index value $AOI_{mean}$, or a graphical representation of said at least one index value AOI or mean index value $AOI_{mean}$.

In other words, according to the invention, it is proposed to analyse the variations of the $CO_2$ content values during the chest compressions, to extract from these the maximum $CO_2$ content (Vmax) and minimum $CO_2$ content (Vmin) and to use them to calculate an airway opening index or AOI which is representative of the quality of the cardiac massage and of the level of opening of the airways (alveoli, bronchioles, etc.), thus permitting a better estimation of the quantity and quality of ventilation of these airways. This AOI index and/or mean AOI index $AOI_{mean}$ can then be displayed on a GUI in the form of a numerical value, for example a percentage, or in the form of a graphical representation, such as a curve or preferably a pictogram or similar.

For example, the AOI index during a chest compression is equal to:

1 (or 100%) when the minimum $CO_2$ content value Vmin is zero $CO_2$ (or 0 mmHg), which corresponds to fully open airways in the patient, and 0 (or 0%) when there is no $CO_2$ variation, that is to say when Vmax is equal to Vmin. This corresponds to closed airways.

between 0 and 1, for intermediate minimum $CO_2$ content values, corresponding to airways more or less open or closed.

It will be immediately appreciated that knowing this AOI index, and therefore being able to know in real time the state of the airways of the patient being treated, is of great use to the first responder performing the CPR. Using a display such as a pictogram (i.e. drawing, icon or the like) is particularly expedient since it allows the user to easily and immediately visualize the state of the airways of the patient.

It will be noted that, by convention in the medical field, $CO_2$ contents are expressed in the form of $CO_2$ partial pressure, that is to say preferably in mmHg, or in kPa; however, they could also be expressed in another unit (e.g. % by volume, molar %, etc.).

Depending on the case, the monitoring and/or respiratory assistance apparatus according to the invention may comprise one or more of the following technical features:

the signal-processing and control means are configured to:

i) determine several maximum $CO_2$ content values (Vmax) and several minimum $CO_2$ content values (Vmin) during the durations (dt) of several successive chest compressions (i.e. contractions), ii) calculate the successive opening indices AOI corresponding to said several maximum $CO_2$ content values (Vmax) and several minimum $CO_2$ content values (Vmin), and iii) calculate a mean index $AOI_{mean}$ on the basis of the successive AOI indices obtained for the n chest compressions.

the signal-processing means are configured to calculate a mean index $AOI_{mean}$ on the basis of the successive AOI indices obtained for n chest compressions, such that:

$$AOI_{mean} = \Sigma_{i=1}^{n} AOI(i)/n$$

where: n is an integer of CC, with n>1.

preferably, the signal-processing means are configured to determine the maximum $CO_2$ content values (Vmax) and minimum $CO_2$ content values (Vmin) during the duration (dt) of each chest compression.

the signal-processing means are configured to transmit to the GUI at least one calculated AOI index value or at least one calculated mean AOI index value $AOI_{mean}$, and the graphical user interface is configured to display said at least one AOI value or mean AOI value $AOI_{mean}$.

the GUI is configured to display at least one AOI value or mean AOI value $AOI_{mean}$ in the form of a numerical value, in particular a value expressed as a percentage (%).

alternatively, the GUI is configured to display at least one AOI value or mean AOI value $AOI_{mean}$ in the form of a graphical representation, for example a pictogram, a curve, a bar graph, a pie chart or any other representation.

preferably, the GUI is configured to display at least one AOI value or mean AOI value $AOI_{mean}$ in the form of at least one pictogram, that is to say a drawing, an icon or the like. For example, the pictogram can represent lungs of variable/different size depending on the AOI value or mean AOI value $AOI_{mean}$. In this example, the higher the AOI value or the mean AOI value $AOI_{mean}$, thus representing substantial opening of the airways of the patient, the more the displayed pictogram (i.e. lungs) will be of a considerable size (i.e. dimension) on the GUI, and conversely. The pictogram will also be able to be displayed in different colours depending on said AOI value or mean AOI value $AOI_{mean}$, or in both different sizes and different colours depending on the index.

the means for measuring the $CO_2$ content comprise a capnometer or any other $CO_2$ sensor.

the means for measuring the $CO_2$ content are configured to perform $CO_2$ content measurements continuously.

the signal-processing means comprise at least one microprocessor, in particular a microcontroller, using at least one algorithm.

the signal-processing means comprise at least one electronic board.

it comprises alarm means configured to trigger when an index value AOI or mean index value $AOI_{mean}$ is below a given threshold, preferably when AOI<0.75 (i.e. <75%) or $AOI_{mean}$<0.75 (i.e. <75%).

the alarm means comprise an acoustic or visual alarm.

the alarm means comprise a visual alarm, and the GUI is configured to display said visual alarm, for example an indicator light or similar.

the GUI comprises a digital (i.e. numerical) screen, preferably a touch screen.

the screen comprises several touch controls that activate different functions and/or several display zones or windows.

the screen is of the type with colour display.

alternatively, the screen is of the type with black and white display or permits a change-over from colour display to black and white display in order to save energy.

it comprises storage means for storing (i.e., recording) the maximum $CO_2$ content values (Vmax) and/or the minimum $CO_2$ content values (Vmin).

it comprises storage means cooperating with the signal-processing means.

the storage means comprise a flash memory or hard disk memory.

it comprises storage means for storing (i.e. recording) the AOI values or mean AOI values $AOI_{mean}$.

according to a first embodiment, it is chosen from among cardiac monitoring apparatuses, namely cardiac monitors or cardiac monitors/defibrillators, able to measure and display measurements of one or more physiological parameters or vital signs of the patient, especially cardiac signs, for example the electrical cardiac activity, i.e. electrocardiogram (ECG), and/or the heart rate of the patient, which are measured by electrodes placed on the patient; the oxygen saturation SpO2 of the patient, measured via a transcutaneous sensor; the temperature via a temperature sensor in contact with the body of the patient, and/or the arterial pressure (AP) by means of an arterial pressure measurement cuff.

it is a cardiac monitoring apparatus comprising means for measuring heart activity that are configured to perform measurements continuously, in particular several electrodes placed on the body of the patient. Preferably, the electrodes are connected electrically to the signal-processing means and transmit cardiac signals to the latter, that is to say signals of measurement of the cardiac activity of the patient, in particular the electrical activity of the patient's heart.

the signal-processing means are configured to process the cardiac signals originating from the means for measuring the cardiac activity of the patient.

the GUI is configured to display the cardiac activity of the patient corresponding to the processed cardiac signals, in the form of at least one numerical value or a graphical representation, in particular a curve.

the means for measuring the cardiac activity of the patient are configured to measure the heart rate, the cardiac rhythm and/or the cardiac electrical activity (ECG) of the patient.

it additionally comprises means for measuring the oxygen saturation ($SpO_2$) of the patient, for example a transcutaneous sensor, it additionally comprises means for measuring the body temperature of the patient, for example a temperature sensor in contact with the body of the patient.

it additionally comprises means for measuring the arterial pressure (AP), for example an arterial pressure measurement cuff.

the means for measuring the cardiac activity of the patient are designed to be able to deliver at least one electric shock to the patient, via one or more electrodes placed on the patient.

alternatively, according to a second embodiment, it is chosen from among the assisted ventilation apparatuses, i.e. medical ventilators, comprising a source of respiratory gas, in particular air.

the source of respiratory gas is a motorized micro-blower, also called a turbine or compressor, delivering air, possibly enriched with oxygen.

generally, the $CO_2$ is produced by the patient, that is to say it is observable during the exhalation by the patient, or at the following inhalation when it is reinhaled $CO_2$.

the means for measuring the $CO_2$ content are arranged in such a way as to perform measurements of the $CO_2$ concentration in a gas conduit fluidically connecting the monitoring and/or respiratory assistance apparatus to the patient.

the means for measuring the $CO_2$ content are connected electrically to the signal-processing means.

the source of respiratory gas is in fluidic communication with a gas conduit through which the respiratory gas is conveyed to the patient, i.e. as far as a respiratory interface.

the gas conduit is in fluidic communication with a respiratory interface, also called a patient interface.

the respiratory interface is an endotracheal intubation tube, a face mask or a laryngeal mask, also called a supraglottic device, or any device suitable for administering gas.

the respiratory interface is preferably an endotracheal intubation tube, commonly called a "tracheal tube".

the means for measuring the $CO_2$ content are arranged upstream from and in immediate proximity to the respiratory interface, that is to say near the patient's mouth.

according to a first embodiment, the means for measuring the $CO_2$ content are arranged on a junction piece arranged upstream from the respiratory interface, preferably between the respiratory interface and the downstream end of the gas conduit, in particular between the respiratory interface and a Y-shaped piece comprising internal passages for gas.

preferably, the means for measuring the $CO_2$ content are arranged on a junction piece comprising an internal passage for gas.

according to a second embodiment, the means for measuring the $CO_2$ content are arranged in the apparatus, that is to say in the framework of the apparatus, and are connected, via a gas sampling conduit or similar, to a gas sampling site situated upstream from and in immediate proximity to the respiratory interface.

in particular, the means for measuring the $CO_2$ content are connected fluidically to a gas sampling site carried by a junction piece, in particular arranged between the respiratory interface and the gas conduit, typically between the respiratory interface and a downstream end of said gas conduit.

the junction piece is attached fluidically between the intermediate attachment piece, that is to say a Y-shaped piece, and the respiratory interface, typically a tracheal tube or a mask.

it comprises a patient circuit comprising an inhalation branch through which gas can be conveyed to the patient.

the patient circuit additionally comprises an exhalation branch for discharging the gas exhaled by the patient.

the inhalation branch, the exhalation branch and the respiratory interface are in fluidic communication with each other.

the inhalation branch, the exhalation branch and the patient interface are connected fluidically and/or mechanically, directly or indirectly, to the intermediate attachment piece, in particular a Y-shaped piece.

the means for measuring the $CO_2$ content are arranged in such a way as to perform $CO_2$ concentration measurements at the inlet of the exhalation branch or at the outlet of the inhalation branch of the gas circuit.

the exhalation branch communicates fluidically with the atmosphere in order to discharge all or some of the gas exhaled by the patient, in particular the gas rich in $CO_2$.

the inhalation branch and/or the exhalation branch comprise flexible hoses.

preferably, all or part of the gas conduit forming all or part of the inhalation branch of the gas circuit is a flexible hose.

it comprises control means configured to control the source of respiratory gas and to deliver the respiratory gas in successive ventilatory cycles.

each ventilatory cycle comprises a phase LP during which the gas is delivered by the micro-blower at a low pressure (LP), and a phase HP during which the gas is delivered by the micro-blower at a high pressure (HP), with HP>LP.

the micro-blower is controlled to deliver gas at a low pressure (LP) of between 0 and 20 cm of water, preferably between 0 and 15 cm of water, more preferably between 0 and 10 cm of water.

the micro-blower is controlled to deliver gas at a high pressure (HP) of between 5 and 60 cm of water, preferably between 5 and 45 cm of water, more preferably between 5 and 30 cm of water (with HP>LP).

the phase LP has a duration longer than the phase HP.

the phase LP has a duration of between 2 and 10 seconds, typically of the order of 3 to 6 seconds.

the phase HP has a duration of between 0.5 and 3 seconds, typically of the order of 1 to 2 seconds.

the given time period (dt) is of several seconds.

the time period (dt) is between 2 and 10 seconds, typically of the order of 3 to 6 seconds.

the time period (dt) corresponds to the duration of the phase LP of each ventilatory cycle.

the total duration of a ventilatory cycle is between 3 and 10 seconds.

the given time period (dt) encompasses several durations of successive chest compression and relaxation, typically between 5 and 12 chest compressions.

it comprises a source of electric current, for example a battery or similar, preferably a rechargeable battery.

it comprises a rigid external framework or shell.

the rigid framework is formed wholly or partly of polymer.

the GUI is arranged in one of the walls of the framework.

it additionally comprises a human-machine interface of HMI for inputting, modifying/adjusting, selecting, etc., one or more ventilation parameters, for example the pressures, durations, etc.

the HMI comprises adjustment means, for example one or more buttons, keys, cursors or the like.

BRIEF DESCRIPTION OF THE DRAWINGS

The invention will now be better understood from the following detailed description given as a non-limiting example and with reference to the appended figures, in which.

DETAILED DESCRIPTION OF THE PREFERRED EMBODIMENTS

Figure 1:
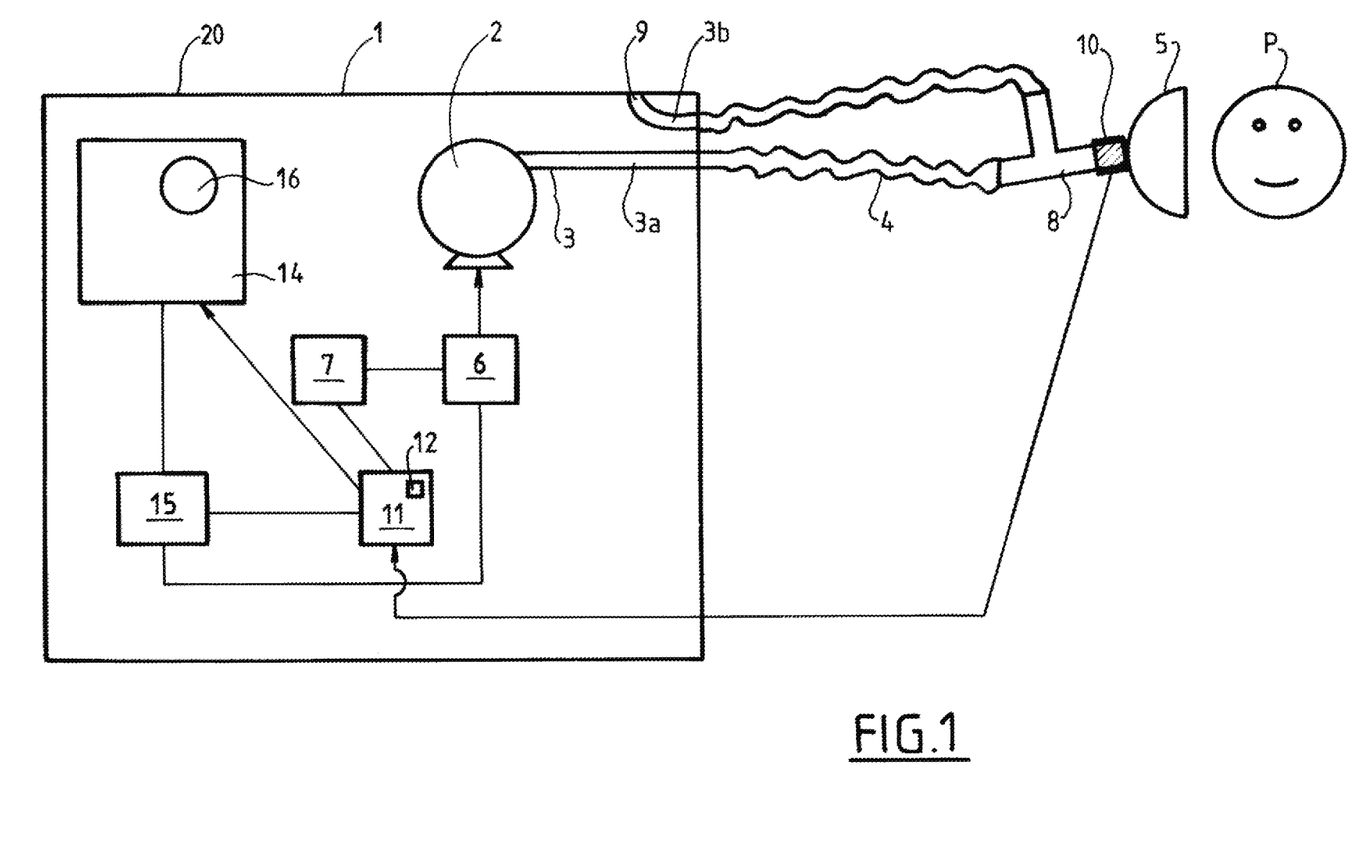
FIG. 1 is a schematic view of a monitoring and respiratory assistance apparatus according to the invention.

FIG. 1 is a schematic representation of an embodiment of a respiratory assistance apparatus or medical ventilator according to the invention used for delivering a respiratory gas, typically air or oxygen-enriched air, to a patient P during cardiopulmonary resuscitation (CPR), that is to say to a person who is in cardiac arrest and on whom a first responder performs cardiac massage, that is to say an alternation of chest compressions (CC) and relaxations (R), that is to say non-compressions.

This apparatus or ventilator 1 comprises a source 2 of respiratory gas, such as a motorized micro-blower, which is in fluidic communication with a gas conduit 3 for delivering the respiratory gas to the patient P during cardiopulmonary resuscitation, typically pressurized air, for example via flexible conduit 4 and a gas distribution respiratory interface 5, for example a respiratory face mask or laryngeal mask, a tracheal tube or the like.

The source 2 of respiratory gas is governed, that is to say controlled, by signal-processing and control means 6, in particular an electronic board with microprocessor or similar. The control means 6 control the source 2 of respiratory gas in such a way that it delivers the gas in accordance with one or more predefined ventilation modes that are stored in a memory 7, for example in accordance with a "normal" ventilatory mode, corresponding to ventilation of a patient who is not or no longer in cardiac arrest, and a "CPR" ventilatory mode corresponding to ventilation of a patient who is in cardiac arrest and on whom a first responder initiates or performs CPR.

For example, in accordance with a ventilatory mode intended for CPR, the source 2 of respiratory gas is controlled so as to deliver air in a ventilatory cycle comprising several pressure levels or of the BiPAP type, in particular two pressure levels comprising a low pressure level, for example a low pressure (LP) of between approximately 0 cm $H_2O$ and 15 cm $H_2O$, and a high pressure level, for example a high pressure (HP) of between approximately 7 cm $H_2O$ and 40 cm $H_2O$. The gas is delivered alternately between these two pressure levels (LP, HP) throughout the CPR performed by the first responder, that is to say while the first responder performs the chest compressions and relaxations. The duration ($D_{LP}$) of delivery of gas at low pressure (LP) by the micro-blower 1 is between 2 and 10 seconds, typically of the order of 3 to 6 seconds, whereas the duration ($D_{HP}$) of delivery of gas at high pressure (HP) is less than 3 seconds, for example of the order of 0.5 to 1.5 seconds.

The micro-blower 1 of the ventilator generates two pressure levels, namely a high pressure level (i.e. HP) and a low pressure level (i.e. LP). The cardiac massage alternating between phases of chest compression (CC) and relaxation generates pressure peaks, which are superposed on the pressure cycles of the ventilator. This results in pressure peaks at the high plateaus (i.e., at HP) and low plateaus (i.e. at LP) which reflect the chest compressions with increased pressure, since the chest yields under the pressure of the chest compressions performed by the first responder, and the relaxations with low pressure, since the chest rises again in the absence of chest compressions.

The air delivered by the micro-blower 2 is conveyed through the gas conduit 3 which forms all or part of the inhalation branch 3a of the patient circuit of the ventilator 1.

The gas conduit 3 is in fluidic communication with the respiratory interface 5, via the flexible tubing 4, in such a way as to deliver to it pressurized air originating from the micro-blower 2. The gas conduit 2 will be attached to the respiratory interface 5 by way of an intermediate attachment piece 8, here a Y-shaped piece. This Y-shaped intermediate attachment piece 8 comprises internal gas passages and is moreover attached to an exhalation branch 3b of the patient circuit of the ventilator 1, so as to be able to collect and convey the gases rich in $CO_2$ that are exhaled by the patient and to discharge them to the atmosphere (at 9).

Also provided are means 10 for measuring the $CO_2$ content, called a $CO_2$ sensor 10 or capnometer, which means are designed to perform measurements of the concentration of $CO_2$ in the gases exhaled by the patient P and to deliver $CO_2$ content measurement signals to signal-processing means 11 where these measurement signals can be processed, in particular by one or more calculation algorithms or similar.

In the embodiment in FIG. 1, the $CO_2$ sensor 10 is arranged near the mouth of the patient P in the mainstream configuration, that is to say upstream from and in immediate proximity to the respiratory interface 5, preferably between the Y-shaped piece 8 and the respiratory interface 5, e.g. a tracheal tube.

However, the $CO_2$ sensor 10 may also be arranged in the sidestream configuration, for example in the framework 20 of the respiratory assistance apparatus 1 and is connected, via a gas sampling line, such as tubing or the like, to a gas sampling site situated upstream from and in immediate proximity to the respiratory interface 5, for example on the junction piece 18. This gas sampling line allows gas to be sampled and then conveyed to the $CO_2$ sensor 10.

The $CO_2$ sensor 10 performs continuous measurements of the concentration of $CO_2$ in the gases expired by the patient P, in particular the gas flowing through the Y-shaped piece 8, which gas is enriched in $CO_2$ during its passage through the lungs of the patient P, where gaseous exchanges take place.

The $CO_2$ content measurement signals are then transmitted by the $CO_2$ sensor 10 to the signal-processing means 11 via an electrical connection 13 or similar, in particular by wires or the like, which signal-processing means (11) preferably comprise an electronic board 12 with a microprocessor, preferably with a microcontroller, using one or more algorithms.

Preferably, the signal-processing means 11 are connected electrically to the storage means 7, for example a memory card or similar, so as to be able to record there all or some of the $CO_2$ content values measured over time, in particular during the chest compressions.

It will be noted that, depending on the embodiment chosen, the signal-processing means 11 and the control means 6 can be combined, arranged on or comprise one and the same electronic memory card, or they can be arranged on or comprise separate electronic cards.

In the context of the present invention, the monitoring of an AOI index is of great importance since the first responder is thereby informed in real time of the opening or non-opening of the airways and thus knows whether or not the successive chest compressions performed generate a ventilation flowrate in the patient P.

More precisely, the signal-processing means 11 are configured to:

a) determine at least one maximum $CO_2$ content value (Vmax) and at least one minimum $CO_2$ content value (Vmin), during at least one duration (dt) of at least one chest compression (CC), and b) one airway opening index AOI such that:

$$AOI=(Vmax-Vmin)/Vmax$$

Preferably, the signal-processing means are configured to:

i) determine several maximum $CO_2$ content values (Vmax) and several minimum $CO_2$ content values (Vmin) during the durations (dt) of n successive chest compressions (with n>1), ii) calculate the successive opening indices AOI, as above, corresponding to the maximum $CO_2$ content values (Vmax) and several minimum $CO_2$ content values (Vmin), and iii) calculate a mean index $AOI_{mean}$ on the basis of the successive AOI indices obtained for the n chest compressions, with: $AOI_{mean}=\Sigma_{i=1}^{n}AOI(i)/n$ where: n is an integer of CC, with n>1.

The storage means 7 can also record all or some of the values of the AOI index and of the mean AOI index $AOI_{mean}$ calculated by the signal-processing means 11.

More generally, it has been found in practice that the indices AOI and preferably $AOI_{mean}$ reflect the opening of the patient's airways, during the cardiac massage, and inform the first responder(s) in real time of the opening or non-opening of these airways. This information is very useful to the first responder in order to ascertain whether the air insufflation performed during the cardiac massage is effective or not, that is to say whether or not air is reaching the small intrapulmonary airways To this end, the apparatus 1 of the invention additionally comprises at least one graphical user interface or GUI 14, such as a digital screen (e.g. colour, black and white, or both), preferably a touch screen, connected electrically to the signal-processing means 11 which are configured to transmit to the GUI 14 the one or more values of the index AOI or of the mean index $AOI_{mean}$ that have been calculated as explained above.

The GUI 14 for its part is configured to display this value of the index AOI or of the mean index $AOI_{mean}$. In other words, the GUI 14 displays the index either in the form of a numerical value, preferably expressed as a percentage, or in the form of one or more graphical representations 16, or both. Examples of a graphical representation 16 include a pictogram, that is to say a drawing or the like, a bar graph, a curve, a pie chart, for example an icon or the like which represents lungs and whose size and/or colour varies depending on the value of the index AOI or $AOI_{mean}$ that has been determined.

The graphical representation 16 can be different depending on the value of the index displayed, in order to facilitate its interpretation or understanding by the first responder, and in particular it can have a size proportional to the value of the index to be displayed and/or a different colour depending on the value of the index to be displayed.

For example, it is possible to display a drawing of the lungs:

of a small size, and for example red in colour, for index values AOI or $AOI_{mean}$ less than a predefined threshold value, for example <0.75 (or 75%), of a medium size, and for example orange in colour, for index values AOI or $AOI_{mean}$ between 0.75 and 0.9 (or 75% to 90%), and of a large size, and for example green in colour, for index values AOI or $AOI_{mean}$ greater than a predefined upper threshold value, for example >0.9 (or 90%).

It is also possible to provide acoustic or visual alarm means configured to trigger when an index value AOI or a mean index value $AOI_{mean}$ is less than a given alarm threshold, preferably when AOI<0.75 (i.e. <75%) or $AOI_{mean}$<0.75 (i.e. <75%), preferably a visual alarm, and the GUI 14 is configured to display said visual alarm.

A source 15 of electric current, such as a rechargeable battery or similar, directly or indirectly supplies electric current to the signal-processing means 11 and the control means 6, the micro-blower 2, the GUI 14 or any other element of the apparatus, in particular the storage means 7. The source 15 of electric current is preferably arranged in the framework 20 of the ventilator.

The apparatus 1 according to the present invention is particularly suitable for use during cardiopulmonary resuscitation (CPR) on a person (i.e., a patient) in cardiopulmonary arrest, in the context of which a respiratory gas such as pressurized air is supplied, in accordance with a ventilatory cycle with several pressure levels, to said person undergoing the cardiac massage with alternating chest compressions and relaxations. To facilitate its transport by the first responders, for example by a physician, a nurse, a fire-fighter or similar, the ventilator of the invention is preferably arranged in a bag for carrying it.

The apparatus 1 according to the present invention can be a medical ventilator, as described above, or a monitor or a combined cardiac monitor/cardiac defibrillator for additionally monitoring the cardiac activity of the patient, especially via electrodes, and optionally delivering electric shocks.

Figure 2:
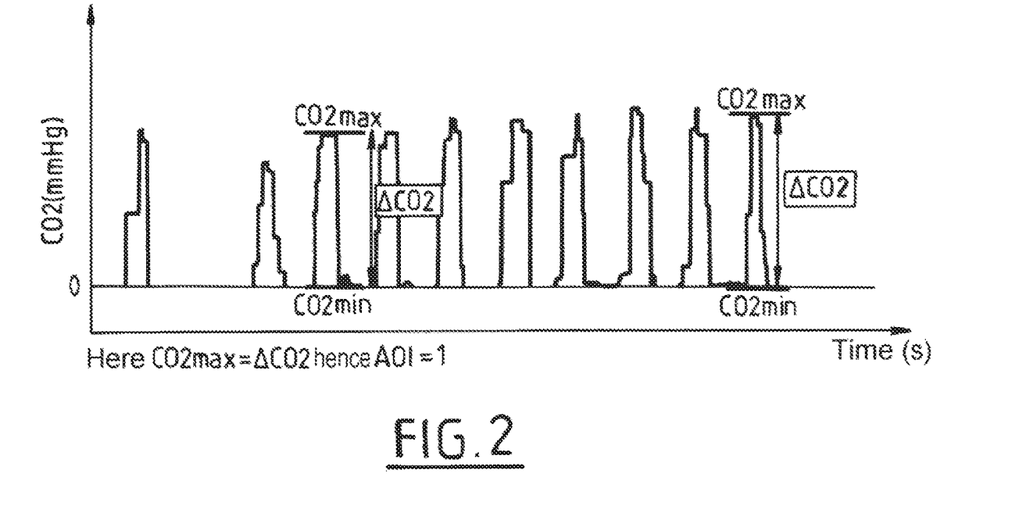
FIG. 2 is an example of a curve of the $CO_2$ content over time, corresponding to airways that are well open.
Figure 3:
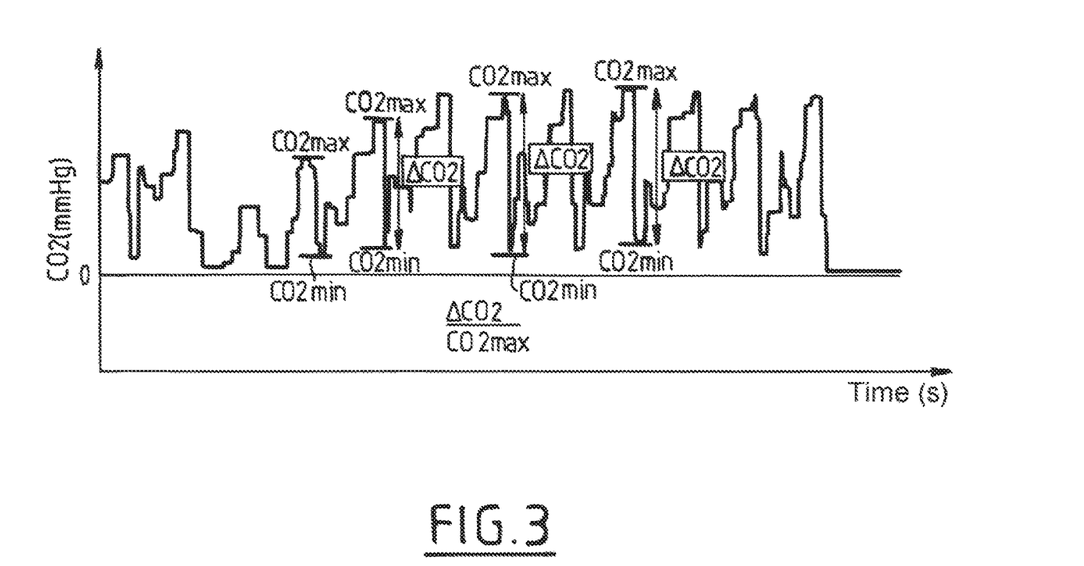
FIG. 3 is similar to FIG. 2 but corresponds to airways that are a little less open than in the case of FIG. 2.
Figure 4:
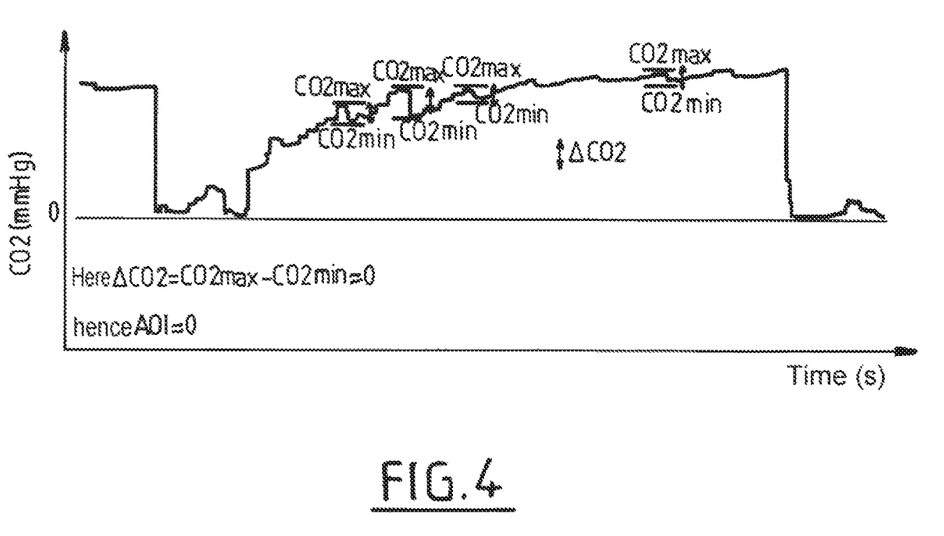
FIG. 4 is similar to FIG. 2 but corresponds to airways that are closed or just slightly open.

FIGS. 2 to 4 illustrate the present invention.

More precisely, FIGS. 2 and 3 are examples of $CO_2$ content curves over time, corresponding to airways that are fully open (FIG. 2) or to airways that are almost fully open (FIG. 3), that is to say very slightly closed in relation to those of FIG. 2.

As will be seen, these curves comprise $CO_2$ peaks which are produced during the chest compressions performed by the first responder on the patient P during the cardiac massage. The $CO_2$ content is expressed here in mmHg, i.e. partial $CO_2$ pressure (mmHg) in the gas; however, the $CO_2$ content could be expressed with another magnitude, for example a % by volume, a molar % or the like.

Each $CO_2$ content peak is characterized by a high value ($CO_2$ max) and a low value ($CO_2$ min) corresponding to the maximum $CO_2$ content value (Vmax) and minimum $CO_2$ content value (Vmin) that are used to determine the indices AOI and $AOI_{mean}$. The amplitude $\Delta CO_2$ of each peak corresponds to the difference Vmax–Vmin during each chest compression performed during the cardiac massage.

In FIG. 2, the minimum $CO_2$ content value is equal to 0, hence the index AOI is equal to 1, or 100%, which corresponds to fully open airways, for which the gas transfers are optimal in the patient's lungs.

Moreover, in FIG. 3, it will be seen that in this case the minimum $CO_2$ content value is close to 0, hence the index AOI is close or very close to 1, for example of the order of approximately 90 to 99%, which corresponds to airways that are almost fully open, for which the gas transfers are still very good.

Conversely, FIG. 4 illustrates a $CO_2$ curve obtained for a patient with closed airways, for which the gas exchanges are poor. As will be seen, in this case the amplitude $\Delta CO_2$ of each peak, which corresponds to the difference Vmax–Vmin, is very small, that is to say the high ($CO_2$max) and low ($CO_2$min) values are close, hence the difference (Vmax-Vmin) tends towards 0. In this case, there is a low AOI index value, for example below 0.2 (i.e. <20%).

It will be immediately appreciated that, by providing the first responder with this AOI index value for each peak, that is to say each chest compression, or a mean value AOImean over several chest compressions, that is to say corresponding to several successive peaks, said first responder can immediately have a good idea of the state of opening of the patient's airways and will be able to act accordingly.

Knowing more precisely the state of opening of the airways, i.e. the AOI index according to the invention, the first responder will have better information concerning what is called the "effective" ventilation of the patient, that is to say the quantity of ventilation reaching the alveoli and thus participating in the gas exchanges through the alveolar-capillary membrane of the patient. It is indeed this "effective" ventilation of the patient that permits efficient re-oxygenation of the patient's blood and removal of the $CO_2$ that it contains, by diffusion through the alveolar-capillary membrane of the patient's lungs.

Knowing this AOI index, the user, typically the first responder, can decide to adjust the ventilation by modifying all or some of the ventilation parameters when he ascertains that it is not sufficiently effective, that is to say when the re-oxygenation of the patient's blood is insufficient.

In other words, through knowledge of the AOI index of the invention, the user can carry out different adjustments of the medical device, in particular of the ventilator serving to supply respiratory gas to the patient, in order to perform a ventilation that is as effective as possible for the patient. This information on the state of opening of the airways also allows the first responder to take therapeutic decisions, especially on whether to continue or stop the cardiopulmonary resuscitation (CPR) performed on the patient.

The invention claimed is:

1. A monitoring and/or respiratory assistance apparatus (1) that can be used during a cardiopulmonary resuscitation (CPR) with successive chest compressions of duration (dt) performed on the patient and with relaxations, said apparatus comprising:

a $CO_2$ content measurement sensor (10) configured and adapted for measuring a concentration of $CO_2$ produced by a patient during the cardiopulmonary resuscitation (CPR), and to supply a $CO_2$ content measurement signal to a signal-processing system (11), the signal-processing system (11) configured and adapted to process the $CO_2$ content measurement signal originating from the $CO_2$ content measurement sensor (10), and at least one graphical user interface (GUI) (14), characterized in that the signal-processing system (11) is configured to:

a) determine at least one maximum $CO_2$ content value (Vmax) and at least one minimum $CO_2$ content value (Vmin), during at least one duration (dt) of at least one chest compression (CC), and b) calculate at least:
one airway opening index AOI such that:

$$AOI = (V\text{max} - V\text{min})/V\text{max}$$

Or
a mean index $AOI_{mean}$ on the basis of several successive opening indices AOI obtained during the durations (dt) of n successive chest compressions (with n>1), and c) transmit to said graphical user interface (14) at least one index value AOI or at least one mean index value $AOI_{mean}$, and the graphical user interface (14) is configured to display said at least one index value AOI or mean index value $AOI_{mean}$, or a graphical representation (16) of said at least one index value AOI or mean index value $AOI_{mean}$.

2. The apparatus according to claim 1, characterized in that the signal-processing system (11) is configured to:
   i) determine several maximum $CO_2$ content values (Vmax) and several minimum $CO_2$ content values (Vmin) during the durations (dt) of n successive chest compressions (with n>1),
   ii) calculate the successive opening indices AOI corresponding to said several maximum $CO_2$ content values (Vmax) and several minimum $CO_2$ content values (Vmin), and
   iii) calculate a mean index $AOI_{mean}$ on the basis of the successive AOI indices obtained for the n chest compressions.

3. The apparatus according to claim 1, characterized in that the signal-processing system (11) is configured to calculate a mean index $AOI_{mean}$ on the basis of the successive AOI indices obtained for n chest compressions, such that:

$$AOI_{mean} = \Sigma_{i=1}^{n} AOI(i)/n$$

where: n is an integer of CC, with n>1.

4. The apparatus according to claim 1, characterized in that the graphical user interface (14) is configured to display said at least one index value AOI or mean index value $AOI_{mean}$ expressed in the form of a percentage.

5. The apparatus according to claim 1 characterized in that the graphical user interface (14) is configured to display at least one index value AOI or mean index value $AOI_{mean}$ in the form of a graphical representation (16) chosen from a pictogram, a curve, a bar graph or a pie chart.

6. The apparatus according to claim 1, characterized in that the $CO_2$ content measurement sensor (10) comprises a capnometer configured to perform $CO_2$ content measurements continuously.

7. The apparatus according to claim 1, characterized in that the signal-processing system (11) comprises at least one microprocessor (12) programmed with at least one algorithm.

8. The apparatus according to claim 1, further comprising an alarm configured to trigger when AOI<0.75 (i.e. <75%) or $AOI_{mean}$<0.75 (i.e. <75%).

9. The apparatus according to claim 8, characterized in that the alarm comprises an acoustic or visual alarm, and the GUI (14) is configured to display said visual alarm.

10. The apparatus according to claim 1, characterized in that the graphical user interface (14) comprises a digital screen.

11. The apparatus according to claim 1, characterized in that the apparatus is chosen from among an assisted ventilation apparatus comprising a source (2) of respiratory gas and a micro-blower.

12. The apparatus according to claim 1, characterized in that the apparatus is chosen from among a cardiac monitor or a cardiac monitors/defibrillator.

* * * * *